US008173383B2

(12) United States Patent
Houghton et al.

(10) Patent No.: US 8,173,383 B2
(45) Date of Patent: May 8, 2012

(54) **METHODS AND MATERIALS FOR THE DETECTION OF *LEISHMANIA* INFECTION**

(75) Inventors: Raymond L. Houghton, Seattle, WA (US); Steven G. Reed, Seattle, WA (US); Syamal Raychaudhuri, Seattle, WA (US)

(73) Assignee: InBios International, Inc., Seattle, WA (US)

( * ) Notice: Subject to any disclaimer, the term of this patent is extended or adjusted under 35 U.S.C. 154(b) by 0 days.

(21) Appl. No.: 13/012,398

(22) Filed: Jan. 24, 2011

(65) Prior Publication Data

US 2011/0159528 A1    Jun. 30, 2011

Related U.S. Application Data

(62) Division of application No. 12/096,571, filed as application No. PCT/US2006/061699 on Dec. 6, 2006, now abandoned.

(60) Provisional application No. 60/742,761, filed on Dec. 6, 2005.

(51) Int. Cl.
*G01N 33/53* (2006.01)
*G01N 33/542* (2006.01)
*G01N 33/00* (2006.01)
*A61K 39/00* (2006.01)
*C07K 1/00* (2006.01)
*C07K 14/00* (2006.01)
*C07K 17/00* (2006.01)

(52) U.S. Cl. ........ 435/7.94; 435/7.9; 435/7.92; 435/7.1; 424/184.1; 424/185.1; 424/265.1; 424/269.1; 530/350

(58) Field of Classification Search .................. None
See application file for complete search history.

(56) References Cited

U.S. PATENT DOCUMENTS

| 6,365,165 | B1 | 4/2002 | Reed et al. | |
| 6,720,160 | B2 | 4/2004 | Wolde-Mariam | |
| 2002/0081320 | A1 | 6/2002 | Reed et al. | |
| 2003/0040125 | A1* | 2/2003 | Bernatchez et al. | 436/518 |

FOREIGN PATENT DOCUMENTS

WO    9964864 A1    12/1999

OTHER PUBLICATIONS

Singh, S Sivakumar R, "Recent Advances in the Diagnosis of Leishmaniasis," Journal of Postgraduate Medicine, vol. 49, Issue No. 1, pp. 55-60 (Jan.-Mar. 2003).
Salman, Salah M. et al.,"Cutaneous Leishmaniasis: Clinical Features and Diagnosis," Clinics in Dermatology, vol. 17, pp. 291-296 (1999).
Kelleher, Michelle et al., "Identification of a macrophage-binding determinant on lipophosphoglycan from *Leishmania major* promastigotes," Proc. Natl. Acad. Sci. USA, vol. 89, pp. 6-10 (Jan. 1992).
Brito, Maria Edileuza F. et al., "Identification of Potentially Diagnostic *Leishmania braziliensis* Antigens in Human Cutaneous Leishmaniasis by Immunoblot Analysis," Clinical and Diagnostic Laboratory Immunology, vol. 7, No. 2, pp. 318-321 (Mar. 2000).
Handeman, E. et al., "An amphipathic sulphated glycoconjugate of *Leishmania*: characterization with monoclonal antibodies," The EMBO Journal, vol. 3, No. 10, pp. 2301-2306 (Oct. 1984).
Webb, John R. et al., "Human and Murine Immune Responses to a Novel *Leishmania major* Recombinant Protein Encoded by Members of a Multicopy Gene Family," Infection and Immunity, vol. 66, No. 7 pp. 3279-3289 (Jul. 1998).
Coler, Rhea N. et al., "Immunization with a Polyprotein Vaccine Consisting of the T-Cell Antigens Thiol-Specific Antioxidant, *Leishmania major* Stress-Inducible Protein 1, and *Leishmania* Elongation Initiation Factor Protects against Leishmaniasis," Infection and Immunity, vol. 70, No. 8, pp. 4215-4225 (Aug. 2002).
Campos-Neto, Antonio et al., "Protection against Cutaneous Leishmaniasis Induced by Recombinant Antigens in Murine and Nonhuman Primate Models of the Human Disease," Infection and Immunity, vol. 69, No. 6, pp. 4103-4108, (Jun. 2001).
Definition of Conformational Determinant/Epitope (Cruse, JM and Lewis RE. Illustrated Dictionary of Immunology, 2nd edition, CRC Press, Boca Raton Florida. 2003., p. 46 and p. 166).
Novagen 2002-2003 catalog, p. 192 and p. 199.
Sigma 2002-2003 catalog, p. 2545-2547, p. 2609 and p. 2615-2616.
Definition of Kit -Compact Oxford English Dictionary.k, retrieved May 4, 2010http://www.askoxford.com/concise_oed/kit_1?view, retrieved May 4, 2010.

* cited by examiner

*Primary Examiner* — Oluwatosin Ogunbiyi
(74) *Attorney, Agent, or Firm* — Janet Sleath; Speckman Law Group PLLC (57) ABSTRACT

The present invention provides rapid diagnostic assays for the detection of *Leishmania* which can readily be used in the field, leading to more rapid treatment. In certain embodiments, the inventive assays, including ELISA and lateral flow assays, employ antibodies that may be effectively employed to detect the *Leishmania major* antigen TSA, which is present in both promastigotes grown in culture and in amastigotes. Such assays may be employed to detect the presence of cutaneous leishmaniasis in a subject using scrapings, biopsies, and/or aspirates taken from cutaneous lesions.

20 Claims, 9 Drawing Sheets

FIG. 5A
PROMASTIGOTES

FIG. 5B
AMASTIGOTES

METHODS AND MATERIALS FOR THE DETECTION OF *LEISHMANIA* INFECTION

REFERENCE TO PRIORITY APPLICATIONS

This application is a divisional of U.S. patent application Ser. No. 12/096,571, filed Sep. 30, 2008, now abandoned, which is the US national phase of PCT patent application no. PCT/US2006/061699, filed Dec. 6, 2006, which claims priority to U.S. provisional patent application No. 60/742,761, filed Dec. 6, 2005.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. W81XWH-05-C-0018 awarded by the Department of Defense.

FIELD OF THE INVENTION

The present invention relates generally to the diagnosis of *Leishmania* infection. More specifically, the invention relates to the immunological detection of cutaneous leishmaniasis.

BACKGROUND OF THE INVENTION

*Leishmania* organisms are intracellular protozoan parasites of macrophages that cause a wide range of clinical diseases in humans and domestic animals, primarily dogs. The life cycles of *Leishmania* involves a vertebrate host (e.g., a human) and a vector (a sand fly) that transmits the parasite between vertebrate hosts. In the vector the parasite takes on a characteristic morphological form known as the promastigote, and reproduces asexually in the vector's gut. When the vector bites a vertebrate host, promastigotes are injected into the host. The promastigotes then enter cells of the vertebrate host and change into a form known as the amastigote. The amastigote reproduces in the host's cells and, when the cells eventually die, the amastigotes are released and infect other cells. The symptoms and pathology associated with leishmaniasis result from the amastigotes killing the host's cells.

In some infections, the parasite may lie dormant for many years. In other cases, the host may develop one of a variety of forms of leishmaniasis. For example, leishmaniasis may be manifested as a cutaneous disease, which is a severe medical problem. Several *Leishmania* species are responsible for cutaneous leishmaniasis. In the Middle East and Central Asia the predominant species responsible for cutaneous forms of leishmaniasis are *L. major* and *L. tropica*, with *L. donovani* and *L. infantum* predominantly leading to visceral forms of leishmaniasis. In Iraq *L. major* is the major cause of cutaneous leishmaniasis with most of the reported cases in the army being due to this agent. *L. major* is the primary agent for zoonotic cutaneous leishmaniasis (ZCL). In Afghanistan the primary agent for cutaneous leishmaniasis is *L. tropica* with an active infection rate in Kabul of 2.7%. However areas of Northern Afghanistan are also endemic for *L. major*. *L. tropica* is more frequently associated with anthroponotic cutaneous leishmaniasis (AZL). With the deployment of U.S. troops to the Middle East and Central Asia there has been a significant increase in the number of personnel developing cutaneous leishmaniasis, particularly in Iraq. This has raised the need for a field test to identify the presence of *Leishmania* parasites directly in skin lesions.

Current diagnostic procedures are not readily applicable to field situations and typically require centralized laboratory testing. In particular PCR has gained a forefront in testing for *Leishmania* species involved in cutaneous leishmaniasis. Material from skin scrapings or biopsy is obtained, and DNA extracted and subjected to PCR analysis. New PCR methods are being developed to enable multiple *Leishmania* species to be detected and differentiated in a single assay. Other methods used for identifying parasites include culture from skin biopsy samples, which is time consuming, or light microscopic analysis or histology of thin tissue sections from lesions or biopsies to analyze for the presence of parasites. In the case of visceral leishmaniasis, a rapid diagnostic test is available based on use of the repeat antigen K39 to detect the presence of antibodies to *L. donovani*, *L. chagasi* and *L. infantum* in serum (Scott et al., *Am. J. Trop. Med. Hyg.*, 44:272-277, 1991). A similar assay does not currently exist for *Leishmania* species involved in cutaneous leishmaniasis.

Serodiagnosis looking for specific antibodies in cutaneous leishmaniasis has been attempted with some success using secreted antigens but this test lacks sufficient sensitivity and specificity. More recently, less invasive procedures have been used involving aspirates or scrapings from skin lesions or by using swabs (see, for example, Matsumoto et al., *Trans. R. Soc. Trop. Med. Hyg.* 93:606-7, 1999). These procedures lend themselves to use as collection devices for rapid field tests. Rabbit anti gp63 has been used in an indirect immunofluorescence assay for detection of *Leishmania* promastigotes and amastigotes in lesion aspirates (Mohareb et al., *J. Egypt Soc. Parasitol.* 28:313-321, 1998). Analysis of Western blot banding patterns has been used in the differential diagnosis of American cutaneous leishmaniasis (Goncalves et al., *Am. J. Trop. Med. Hyg.* 66:91-102, 2002). Skin tests using Leishmanin have also been used to evaluate latent infection but have generally been based on crude lysate antigen preparations and lack specificity (Arana et al., *Trans. R. Soc. Trop. Med. Hyg.* 93:394-6, 1999).

There thus remains a need in the art for a rapid and effective diagnostic test for cutaneous leishmaniasis that may be readily employed in a field situation.

SUMMARY OF THE INVENTION

The present invention provides rapid diagnostic assays for the detection of *Leishmania* amastigotes, promastigotes and/or secreted proteins which can readily be used in the field, leading to more rapid treatment. In one embodiment, the present invention provides diagnostic tests, including ELISA and lateral flow assays, that may be effectively employed to detect a *Leishmania major* antigen that is present in both promastigotes grown in culture and, more importantly, in amastigotes—the form present in cutaneous lesions. Such assays may be employed to detect the presence of cutaneous leishmaniasis in a subject using scrapings, biopsies, and/or aspirates taken from cutaneous lesions. In another embodiment, diagnostic tests, including ELISA and lateral flow assays, are provided that may be effectively employed to detect a *Leishmania major* antigen that is present in secreted proteins and promastigotes but not in amastigotes. Such assays may be employed to detect the presence of cutaneous leishmaniasis in a subject using biological samples such as serum, and scrapings, biopsies, and/or aspirates taken from cutaneous lesions In certain embodiments, the assays disclosed herein employ antibodies specific for the Thiol Specific Antigen (TSA also known as peroxidoxin; SEQ ID NO: 1 and 2). Preferably the antibodies employed in such assays bind to a conformational epitope of TSA that is present in amastigotes. In one embodiment, the assays employ a first TSA-specific antibody as a capture antibody, with a second TSA-specific antibody being employed as a detection antibody. Preferably, the detection antibody is labeled with a reporter group or agent. For example, a monoclonal antibody against TSA, such as the antibody C11C (which was initially raised against amastigotes), may be employed as the capture antibody, with a rabbit polyclonal antibody to recombinant TSA being employed as the detection antibody. In the case of an ELISA, further development of the assay may then be performed using a goat anti-rabbit IgG horseradish peroxidase label. For a lateral flow assay, the anti-TSA antibody is preferably labeled with a colorimetric or fluorescent indicator, such as colloidal gold or a fluorescent dye, thereby allowing a user to determine visually whether a test is positive or negative for cutaneous leishmaniasis.

Dipsticks for use in such lateral flow assays are also provided. In certain embodiments, such dipsticks comprise: (a) a lateral flow membrane; (b) a first area positioned at a first, lower, end of the lateral flow membrane for receiving a test sample, wherein the first area comprises a first antibody specific for a polypeptide of SEQ ID NO: 1, the antibody being labeled with a reporter agent; (c) a second area positioned at a second, upper, end of the lateral flow membrane comprising an immobilized control polypeptide; and (d) a third area positioned between the first and second areas, wherein the third area comprises an immobilized second antibody specific for a polypeptide of SEQ ID NO: 1.

Diagnostic kits comprising such dipsticks are also provided. In certain embodiments, such diagnostic kits comprise a dipstick, a vessel containing lysing buffer, a rod for mixing a biological sample with the buffer to provide a test solution, and a pipette for applying the text solution to the dipstick. Preferably such kits are sealably contained within a container, such as an aluminum pouch, that is generally impermeable to gases and fluids.

In alternative embodiments, the assays for the detection of L. major infection disclosed herein employ an antibody specific for L. major lipophosphoglycan (LPG), such as the monoclonal antibody WIC79.3. Such assays may be in the form of an ELISA or a lateral flow assay as detailed below. Dipsticks for use in such lateral flow assays, and diagnostic kits comprising such dipsticks are also provided.

The above-mentioned and additional features of the present invention and the manner of obtaining them will become apparent, and the invention will be best understood by reference to the following more detailed description. All references disclosed herein are hereby incorporated by reference in their entirety as if each was incorporated individually.

DETAILED DESCRIPTION OF THE INVENTION

In one embodiment, the present invention provides methods and materials for detecting cutaneous leishmaniasis (CL) infection in a biological sample, such as scrapings, biopsies, and/or aspirates, taken from cutaneous lesions of individuals, such as humans and/or other mammals, suspected of being infected with Leishmania. The presence of CL infection may be detected using one or more of the assays described herein to determine the presence or absence of a Leishmania amastigote antigen in a sample. Preferably, the antigen detected using the inventive methods and materials is Thiol Specific Anti-oxidant protein from L. major (TSA; also known as peroxidoxin; Webb et al., Infect. Immun. 66:3279-89, 1998). TSA has previously been shown to induce protection against CL infection in a primate model (Campos-Neto et al., Infect. Immun. 69:4103-4108, 2001). The amino acid sequence for TSA is provided in SEQ ID NO: 1, with the cDNA sequence being provided in SEQ ID NO: 2. In certain embodiments, the inventive assays employ antibodies, either monoclonal or polyclonal, specific for TSA to detect the presence of Leishmania amastigotes in a biological sample. Preferably the antibodies employed in the assays are specific for a conformational epitope of TSA present in amastigotes.

In an alternative embodiment, the present invention provides methods and materials for detecting cutaneous leishmaniasis in a biological sample, such as serum and/or scrapings, biopsies, and/or aspirates taken from cutaneous lesions of individuals, such as humans and/or other mammals, suspected of being infected with Leishmania. In this embodiment, an antibody, such as the monoclonal antibody WIC79.3, is used to detect the presence of an antigen present in L. major secreted proteins and/or promastigotes, but not in L. major amastigotes.

There are a variety of assay formats known to those of ordinary skill in the art for using antibodies to detect an antigen in a sample which may be effectively employed in the inventive methods. See, e.g., Harlow and Lane, *Antibodies: A Laboratory Manual*, Cold Spring Harbor Laboratory, 1988. In one such assay format, an antibody, such as a TSA-specific antibody (referred to as the capture antibody) is immobilized on a solid support (as described below) and contacted with the sample to be tested. After removal of the unbound sample, a second TSA-specific antibody (referred to as the detection antibody), which has been labeled with a reporter group, may be added and used to detect bound antigen. Alternatively, such assays may employ the monoclonal antibody WIC79.3.

In an exemplary competitive assay, the sample may be combined with either a monoclonal or polyclonal antibody, which has been labeled with a suitable reporter group. The mixture of sample and antibody may then be combined with polypeptide antigen immobilized on a suitable solid support. Antibody that has not bound to an antigen in the sample is allowed to bind to the immobilized antigen, and the remainder of the sample and antibody is removed. The level of antibody bound to the solid support is inversely related to the level of antigen in the sample. Thus, a lower level of antibody bound to the solid support indicates the presence of *Leishmania* infection in the sample. To determine the presence or absence of *Leishmania* infection, the signal detected from the reporter group that remains bound to the solid support is generally compared to a signal that corresponds to a predetermined cut-off value. Such cut-off values may generally be determined as described below. Any of the reporter groups discussed below may be used to label the antibodies, and binding may be detected by any of a variety of techniques appropriate for the reporter group employed.

In one embodiment, the inventive assay involves the use of antibody immobilized on a solid support to bind to and remove the antigen from the sample. The bound antigen may then be detected using a detection reagent that binds to the antigen/antibody complex and contains a detectable reporter group. Suitable detection reagents include antibodies that bind to the antigen/antibody complex labeled with a reporter group. Alternatively, a competitive assay may be utilized, in which an antibody that binds to the antigen is labeled with a reporter group and allowed to bind to the immobilized antigen after incubation of the antibody with the sample. The extent to which components of the sample inhibit the binding of the labeled antibody to the antigen is indicative of the reactivity of the sample with the immobilized antibody.

The solid support may be any solid material known to those of ordinary skill in the art to which the fusion polypeptide may be attached. For example, the solid support may be a test well in a microtiter plate, or a nitrocellulose or other suitable membrane. Alternatively, the support may be a bead or disc, formed of glass, fiberglass, latex or a plastic material such as polystyrene or polyvinylchloride. The support may also be a magnetic particle or a fiber optic sensor, such as those disclosed, for example, in U.S. Pat. No. 5,359,681.

The antibody may be bound to the solid support using a variety of techniques known to those in the art, which are amply described in the patent and scientific literature. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of fusion polypeptide ranging from about 10 ng to about 1 μg, and preferably about 100 ng, is sufficient to bind an adequate amount of antigen. Nitrocellulose will bind approximately 100 μg of protein per $cm^3$.

Covalent attachment of the antibody to a solid support may generally be achieved by first reacting the support with a bifunctional reagent that will react with both the support and a functional group, such as a hydroxyl or amino group, on the antibody. For example, the antibody may be bound to supports having an appropriate polymer coating using benzoquinone or by condensation of an aldehyde group on the support with an amine and an active hydrogen on the antibody (see, e.g., Pierce Immunotechnology Catalog and Handbook (1991) at A12-A13).

In certain embodiments, the assay is an enzyme linked immunosorbent assay (ELISA). This assay may be performed by first immobilizing an antibody (referred to as the capture antibody) on a solid support, commonly the well of a microtiter plate. The immobilized antibody is then incubated with the biological sample, and antigen (if present in the sample) is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of *Leishmania* amastigotes, secreted proteins and/or promastigotes within a *Leishmania*-infected sample. Preferably, the contact time is sufficient to achieve a level of binding that is at least 95% of that achieved at equilibrium between bound and unbound antigen. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-antigen complex and that can be detected by any of a variety of means known to those in the art. Preferably, the detection reagent contains a binding agent (such as, for example, Protein A, Protein G, immunoglobulin, lectin or an antibody) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many sources (e.g., Zymed Laboratories, San Francisco, Calif. and Pierce, Rockford, Ill.).

The detection reagent is then incubated with the immobilized antibody-antigen complex for an amount of time sufficient to detect the bound antigen. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of *Leishmania* antigens in the sample, the signal detected from the reporter group that remains bound to the solid support is generally compared to a signal that corresponds to a predetermined cut-off value. This cut-off value is preferably the average 
mean signal obtained when the immobilized antibody is incubated with samples from an uninfected patient. In general, a sample generating a signal that is three standard deviations above the mean is considered positive for *Leishmania* antigens and *Leishmania* infection. In an alternate embodiment, the cut-off value is determined using a Receiver Operator Curve, according to the method of Sackett et al., *Clinical Epidemiology: A Basic Science for Clinical Medicine*, p. 106-7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for *Leishmania* infection.

In one embodiment, the present invention provides an ELISA sandwich assay that may be effectively employed to detect the presence of *Leishmania* amastigotes in samples taken from cutaneous lesions. In this assay, an antibody specific for TSA (referred to as the capture antibody) is coated onto ELISA plates. After blocking, the plates are incubated with the biological sample, washed and then incubated with a second anti-TSA antibody (referred to as the detection antibody), prior to being developed. In a preferred embodiment, the detection antibody is a TSA affinity purified rabbit polyclonal antibody that has been shown to detect TSA in low concentrations of solubilized amastigotes and promastigotes, and the plate is developed using a goat anti rabbit IgG horseradish peroxidase conjugate.

In a second embodiment, the assay is performed in a flow-through or lateral flow format, wherein the anti-TSA antibody is immobilized on a membrane such as nitrocellulose. In the flow-through test, antigens within the sample bind to the immobilized antibody as the sample passes through the membrane. A detection reagent then binds to the antibody-antigen complex as a solution containing the detection reagent flows through the membrane. The detection of bound detection reagent may then be performed as described above. In the lateral flow format, one end of the membrane to which antibody is bound is immersed in a solution containing the biological sample. The sample migrates along the membrane through a region containing the detection reagent, which preferably includes a colorimetric label, such as colloidal gold, and to the area of immobilized capture antibody. Concentration of detection reagent at the capture antibody indicates the presence of *Leishmania* amastigote in the sample. Such tests can typically be performed with a very small amount of biological sample.

Figure 1:
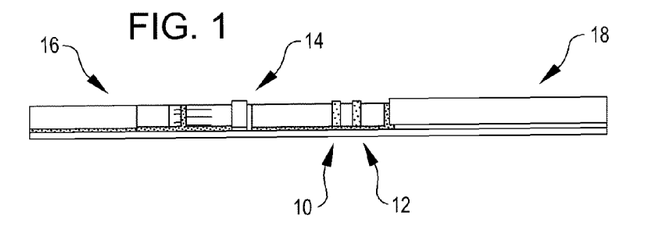
FIG. 1 shows a dipstick for use in a lateral flow assay of the present invention.
Figure 2A:
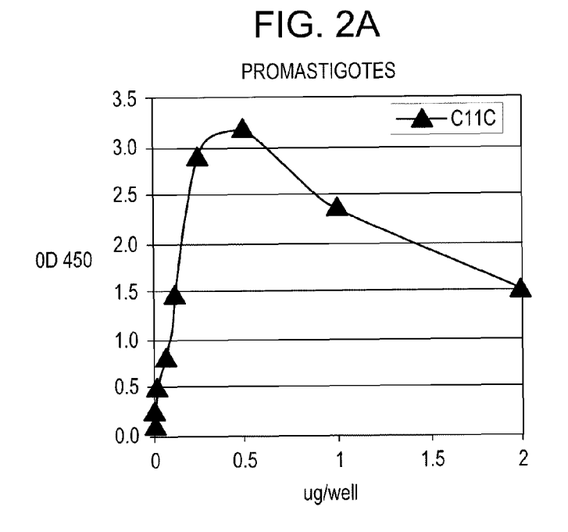
FIGS. 2A and B show the reactivity of the antibody C11C against different concentrations of both promastigotes and amastigotes as determined by ELISA.
Figure 2B:
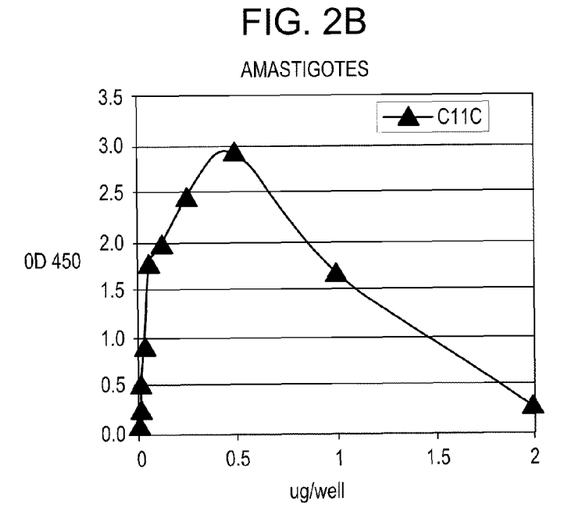
Figure 3A:
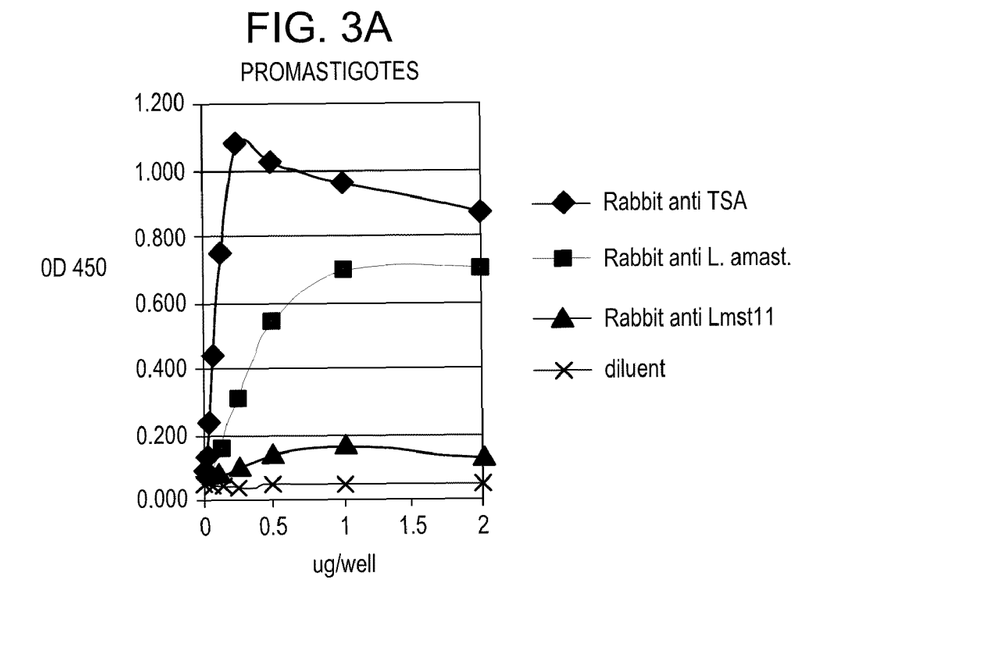
FIGS. 3-5 show the reactivity of various antibodies against promastigotes and amastigotes obtained from mouse skin lesions as determined by ELISA.
Figure 3B:
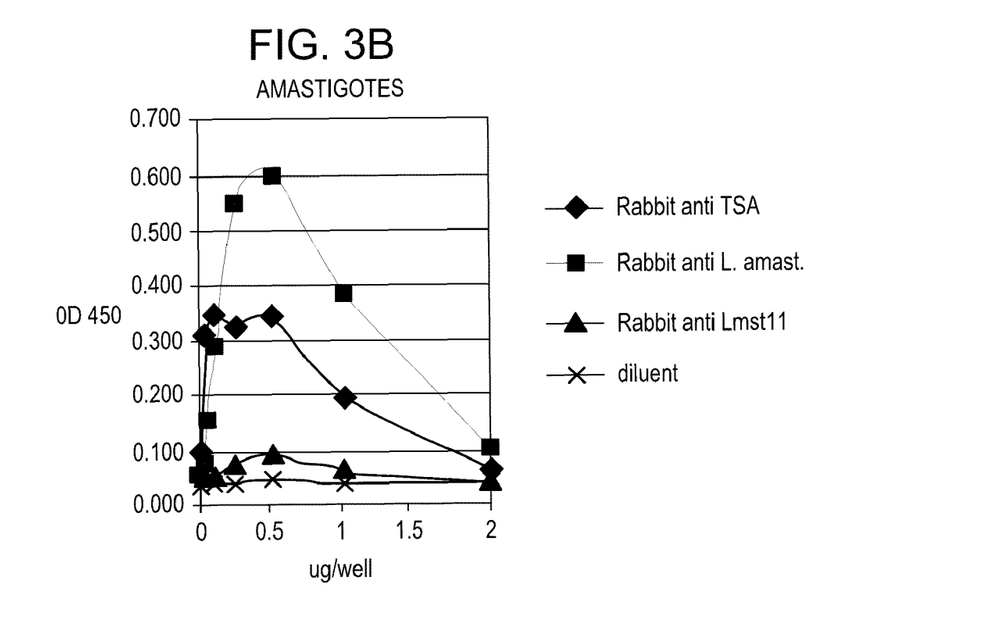
Figure 4A:
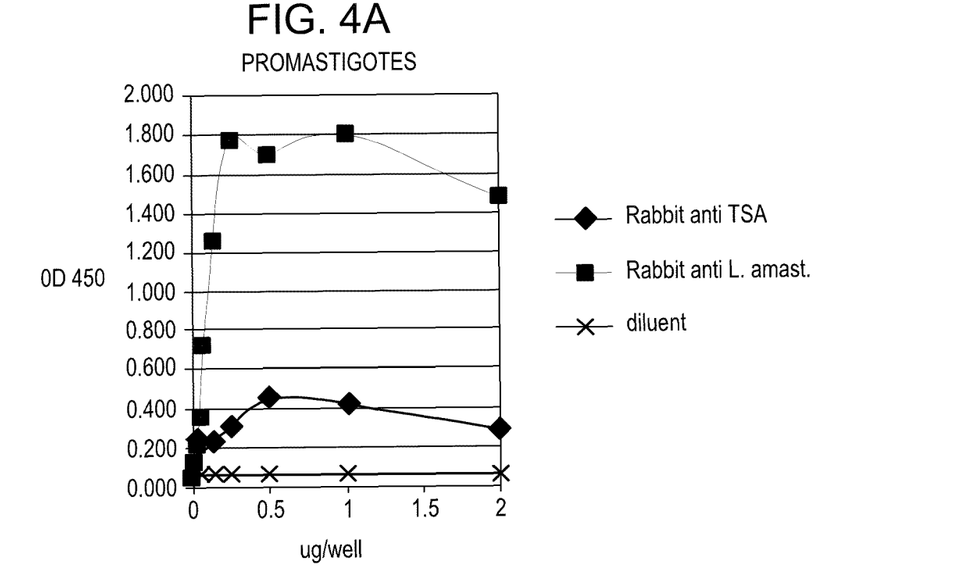
Figure 4B:
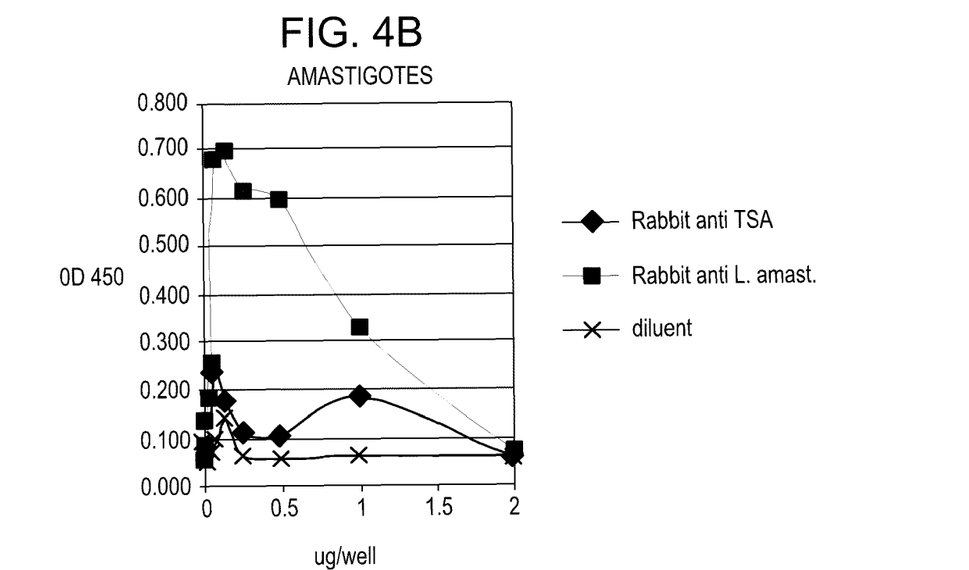
Figure 5A:
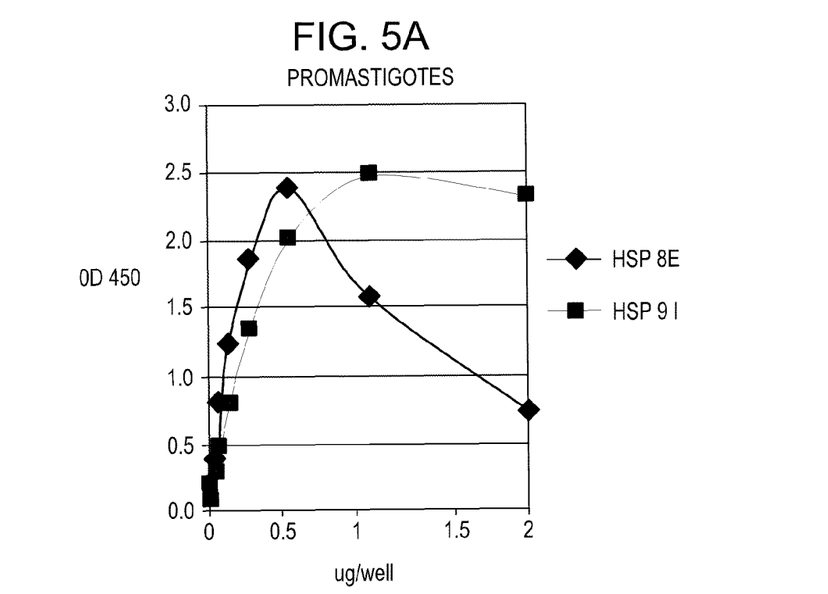
Figure 5B:
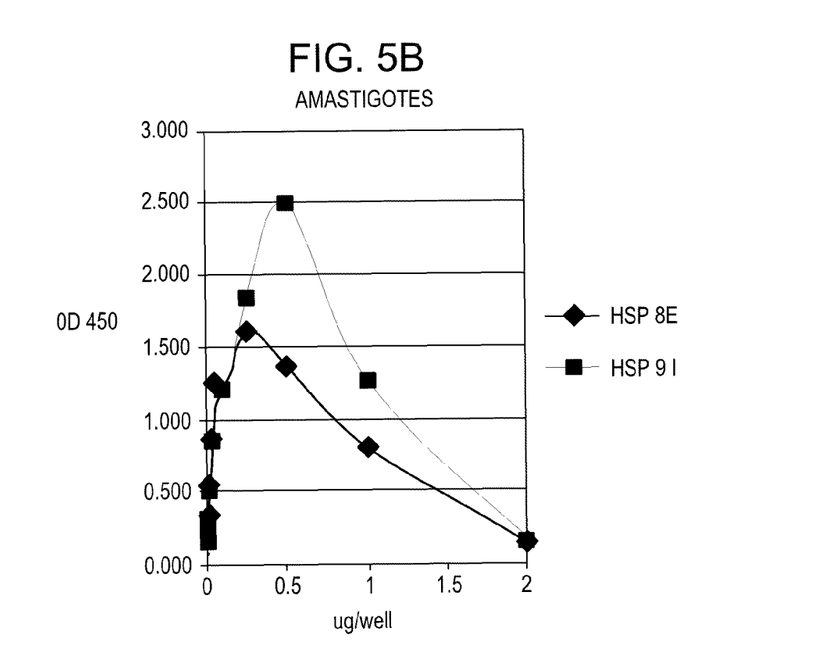

FIG. 1 shows an exemplary dipstick which may be employed in the inventive methods to detect the presence of TSA in a biological sample. In this system, lines are striped (1 μl/cm) on a suitable membrane using an automated biojet system (BioDot, Inc., Irvine, Calif.). The bottom, or test, line 10 consists of a TSA-specific capture antibody in a suitable buffer. One or more test lines can be employed depending on the number of antibodies to be incorporated. The top, or control, line 12 is used as an internal control to make sure that all the test components are working. In this embodiment, control line 12 is protein G or goat anti mouse or rabbit IgG. An anti-TSA antibody ("detection antibody") conjugated to gold is employed as the detection reagent. Colloidal gold consists of discrete, electron-dense, red-colored particles. When concentrated on solid surfaces, these particles can be visually observed. The detection reagent is dried onto a glass fiber pad, or conjugate pad, 14 and laminated below a membrane. Pads that can be effectively employed as conjugate pad 14 include those available from Whatman Inc. (Florham park, NJ), such as the Whatman Rapid Release Pad. A sample pad 16 is soaked in an appropriate buffer, dried and laminated underneath pad 14. Pads that may be effectively employed as sample pad 16 include those available from Ahlstrom Inc. An absorbent top pad 18 is provided to remove excess fluid.

In use, the biological sample is applied onto the end of sample pad 16 and followed with a chase buffer, preferably a phosphate based buffer. The sample mixes with the detection reagent and the resulting complex moves laterally upward and binds to the capture antibody at test line 10 if the sample contains TSA, causing test line 10 to turn red. Unbound complex will continue to travel upwards and will bind to the protein G or goat anti-mouse or rabbit IgG at control line 12 depending on the nature of the antibody chosen for the mobile phase, causing control line 12 to turn red. If a control line is not observed, the test is considered invalid.

Other formats for using monospecific antibodies to detect *Leishmania major* infection in a sample will be apparent to those of ordinary skill in the art.

Assays employing the antibody WIC79.3 to detect the presence of *L. major* secreted proteins or promastigotes may be performed in a similar manner to those employing anti-TSA antibodies.

As noted above, in certain embodiments, the inventive methods employ antibodies, such as polyclonal or monoclonal antibodies, that are specific for the *Leishmania* amastigote antigen TSA. The capture antibody is a preferably a monoclonal antibody specific for TSA. In one embodiment, the monoclonal antibody C11C is employed as the capture antibody. This antibody which, as detailed below, was developed against *Leishmania* amastigotes and has been shown to react with TSA, is available from Dr. Matsumoto, University of Tokyo, Tokyo, Japan. In alternative embodiments, the inventive methods employ the monoclonal antibody WIC79.3, which has been shown to be specific for *L. major* lipophosphoglycan (LPG) (Kelleher et al. *Proc. Natl. Acad. Sci. USA* 89:6-10, 1992; de Ibarra et al. Parasitology 85:523-31, 1982; Greenblatt et al. *J. Clin. Microbiol.* 18:191-3, 1983; Handman et al. *EMBO J.* 1984; 3(10): 2301-6, 1984), and is available from the Walter Reed Army Institute of Research (Silver Spring, Md.).

Antibodies to purified, recombinant or synthesized antigens may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the antigen, such as TSA, may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the antigen may then be purified from such antisera by, for example, affinity chromatography using the antigen coupled to a suitable solid support.

Monoclonal antibodies specific for the antigenic polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation and extraction.

The present invention also provides kits for use in the diagnosis of cutaneous leishmaniasis. Such kits comprise: a dipstick as described above preferably pouched in a generally impermeable container, such as an aluminum foil container, with desiccant; a tube, or vessel, containing lysing buffer; a plastic rod/pestle for mixing skin lesion scrapings/biopsies with the lysing buffer to release amastigotes into solution for testing; and a disposable transfer pipette for applying solution to the dipstick.

The following Examples are offered by way of illustration and not by way of limitation.

Example 1

Preparation of Monoclonal Antibodies to *Leishmania* Amastigotes

Amastigotes for immunization were isolated from nonnecrotic lesions at the dorsal part of the tail base in *L. major* RM2-infected RAG2$^{-/-}$ mice approximately 4 to 5 weeks after infection. The sonicated amastigotes were centrifuged at 1,600 g for 30 min at 4° C. and the resulting supernatants were used as antigens. BALB/c mice were immunized with whole lysate of amastigotes with complete Freund's adjuvant. After the first immunization, the mice were inoculated with the same dose of amastigote homogenate every 3 weeks. The mice were given a final boost of amastigote homogenate 4 days before fusion. Hybrid cells were produced by fusing P3-X63-Ag8-U1 cells with spleen cells isolated from the immunized mice. Hybridomas were screened for production of antibodies against amastigote antigens by ELISA. Limiting dilution was performed twice to obtain monoclonal hybridomas. One of the hybridomas, referred to as C11C, was inoculated into RAG2$^{-/-}$ mice intraperitoneally. After 2 to 3 weeks ascites were harvested and centrifuged, and the supernatant was collected. Immunoglobulins were purified using Protein G.

Example 2

Preparation of Monoclonal and Polyclonal Antibodies to Recombinant TSA

Recombinant TSA expressed in *E. coli* was used as immunogen for preparing additional monoclonal antibodies in mice and for raising a polyclonal antibody in rabbits. Supernatants from four monoclonal antibodies were tested for their reactivity against TSA and an unrelated *T. cruzi* protein as negative control. In addition, the rabbit polyclonal antibody was affinity purified on a TSA sepharose column for use in ELISA and rapid test development.

Example 3

Reactivity of Antibodies Against *L. major* Amastigotes and Promastigotes

Various antibodies, including C11C, were analyzed to determine their reactivity with solubilized preparations of *L. major* promastigotes grown in culture, as well as with amastigotes derived from skin lesions of mice infected with *L. major*. These studies enabled the selection of antibodies/target antigens that reacted with both forms of *L. major* but with particular emphasis on amastigotes, the form present in skin lesions. We initially analyzed antibodies to test their reactivity/titer with a fixed concentration of antigen on an ELISA plate and then, using a fixed dilution, determined what level of antigen could be detected in both *L. major* promastigotes and amastigotes, the latter being derived from skin lesions from infected mice. Polyclonal antibodies used in these initial studies were against *L. major* amastigotes, TSA, LmSTI1 (M15), HSP83 (JV9I), HSP70 (JV8E), LACK antigen and a secreted polyprotein from *L. major* (4A5). LmSTI1 and HSP83 are disclosed in US published patent application no. US 2002/0081320, the disclosure of which is hereby incorporated by reference. Also evaluated were secreted proteins isolated from supernatants of cultured promastigotes of two strains of *L. major, L. tropica* and *L. mexicana* provided by Walter Reed Army Institute of Research (WRAIR).

Table 1 summarizes the reactivity of different antibodies with promastigotes, amastigotes and secreted proteins from *Leishmania* spp., with *L. major* LRC940 and *L. major* Pat2 being different isolates of *L. major*. As shown in Table 1, the C11C antibody and the rabbit anti-TSA antibody showed strong reactivity against both promastigotes and amastigotes as determined by ELISA. FIGS. 2-5 show the reactivity of the various antibodies to both promastigotes and to amastigotes derived from mouse skin lesions. The most reactive antibodies in both promastigotes and amastigotes were the rabbit anti-TSA antibody and the C11C monoclonal antibody to TSA, as well as the rabbit antibody to whole amastigotes. Also strongly reactive were those to the heat shock proteins HSP70 and HSP83 (referred to as HSP 8E and HSP 91, respectively, in FIGS. 5A and B) which may be an alternative to TSA in assay development. LmSTI1, *L. major* polyprotein and LACK were only weakly reactive with both promastigotes and amastigotes.

TABLE 1

| | TSA (C11C Mab) | TSA (pAb) | Rabbit anti Amastigotes | LmSTI1 | HSP70 (8E) (pAb) | HSP83 (9I) (pAb) | LACK (pAb) | 4A5 (pAb) |
|---|---|---|---|---|---|---|---|---|
| Amastigotes | ++++ | ++++ | ++++ | + | ++++ | +++ | + | + |
| Promastigotes Exoantigens | ++++ | ++++ | +++ | + | ++++ | ++++ | + | + |
| L. major LRC940 | ±* | ±* | − | ± | +++ | ++ | ± | + |
| L. major Pat2 | ±* | ±* | − | ± | +++ | ++ | ± | + |
| L. mexicana FD | ±* | ±* | − | ± | +++ | ++ | ± | + |
| L. tropica LRC590 | ±* | ±* | − | ± | +++ | ++ | ± | + |

Example 4

Sandwich ELISA for the Detection of TSA

Figure 6:
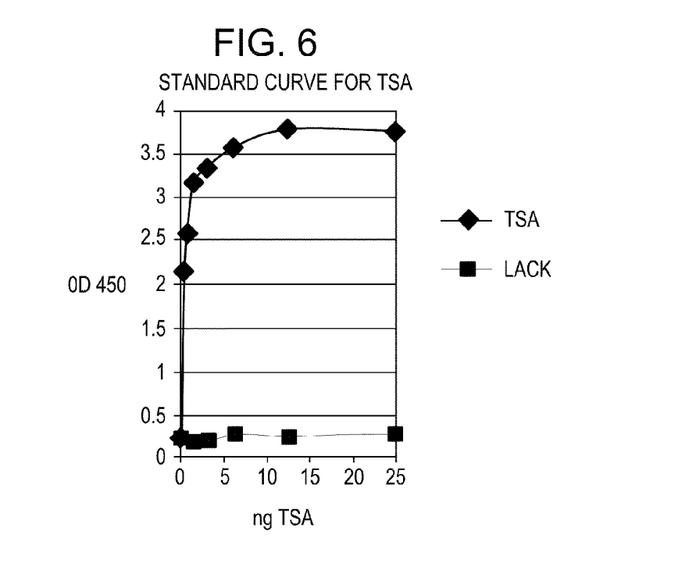
FIG. 6 shows a standard curve for detection of TSA using a sandwich ELISA employing the antibody C11C as the capture antibody and an affinity purified rabbit anti-TSA antibody as the detection antibody. LACK antigen was used as a negative control.
Figure 7:
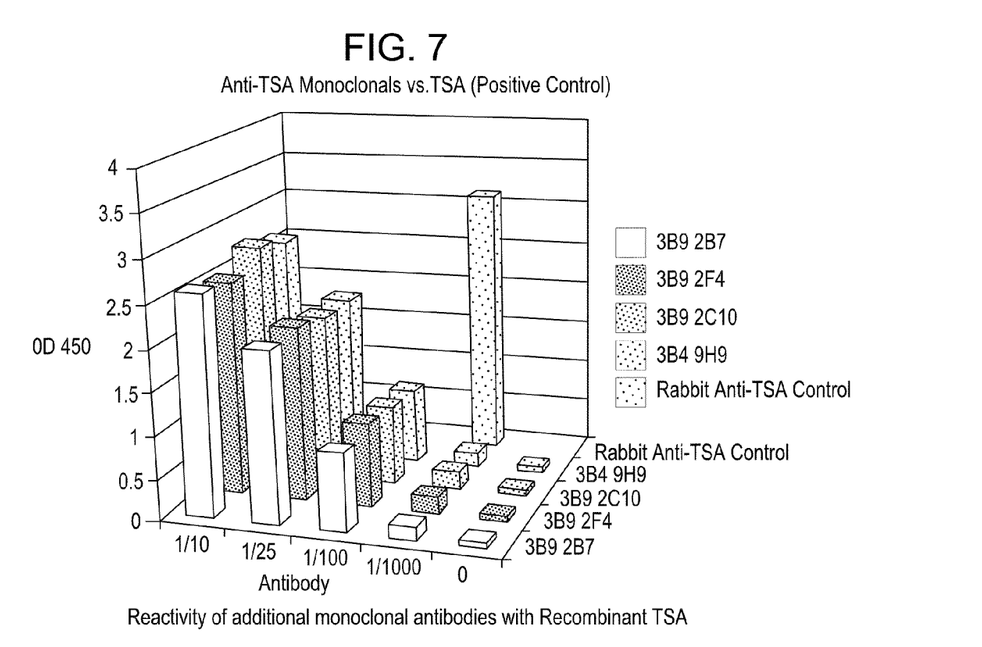
FIG. 7 shows the reactivity of additional monoclonal antibodies to recombinant TSA.
Figure 8A:
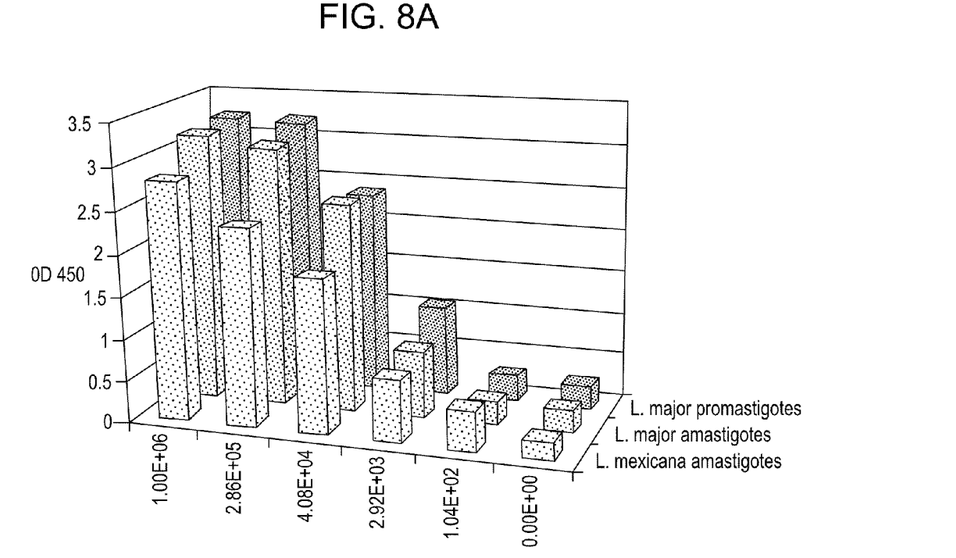
FIGS. 8A and 8B show the ability of the assay of FIG. 6 to detect TSA in cultured L. major promastigotes as well as L. major and L. mexicana amastigotes from infected mice but not in E. coli lysate and exoantigens from various Leishmania spp.
Figure 8B:
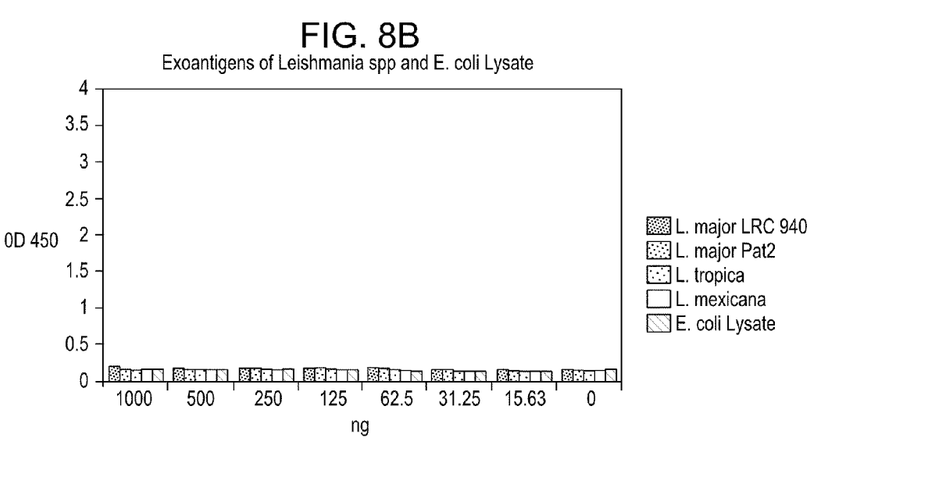

Based on the above studies, a sandwich ELISA assay was established to assess the detectability of TSA in both promastigotes and amastigotes. The monoclonal antibody C11C was coated on the ELISA plate. After blocking, plates were incubated with either purified TSA or different dilutions of promastigotes and amastigotes. After washing, plates were incubated with TSA affinity purified rabbit anti-TSA antibody and finally developed with a goat anti-rabbit IgG horse radish peroxidase conjugate and TMB substrate. The data from these studies is shown in FIGS. 6 and 8. FIG. 6 shows a standard curve for detection of TSA using the sandwich ELISA. Ng levels of antigen were detectable in this assay. FIG. 8 shows the ability of this assay to detect TSA in cultured promastigotes as well as amastigotes, but not in E. coli lysate and an unrelated T. cruzi recombinant protein. FIG. 7 shows the reactivity of four additional monoclonal antibodies raised to recombinant TSA that could potentially replace C11C or the polyclonal antibody to TSA. No reactivity was detected when LmSTI1 was used as target antigen.

The TSA sandwich ELISA was performed as follows. Microtiter plates (Immulon 2, flat bottom, high binding) were coated at 200 ng/well overnight at 4° C. in a carbonate/bicarbonate buffer pH 9.6. After washing three times with phosphate buffered saline containing Tween 20 (0.05%; PBST), the plates were blocked with PBS containing 1% bovine serum albumin and 0.05% Tween 20 for 1 hour. Antigens at desired concentration, or amastigotes or promastigotes solubilized in detergent containing buffer and diluted from known cell concentrations, were then added to the plate and incubated for 30 minutes at 37° C. After washing six times in PBST, TSA affinity purified rabbit anti-TSA was added at 1/1000 dilution and further incubated at 37° C. for 30 min. Plates were again washed six times with PBST and further incubated at 37° C. for 30 minutes with a 1/10,000 dilution of goat anti rabbit IgG (H&L)-horse radish peroxidase labeled (Southern Biotech). After washing six times in PBST, the plate was developed with TMB substrate for 15 min at ambient temperature and stopped with 1N $H_2SO_4$. Plates were immediately read at OD 450 nm.

Example 5

Lateral Flow Immunoassay for the Detection of TSA

Figure 9:
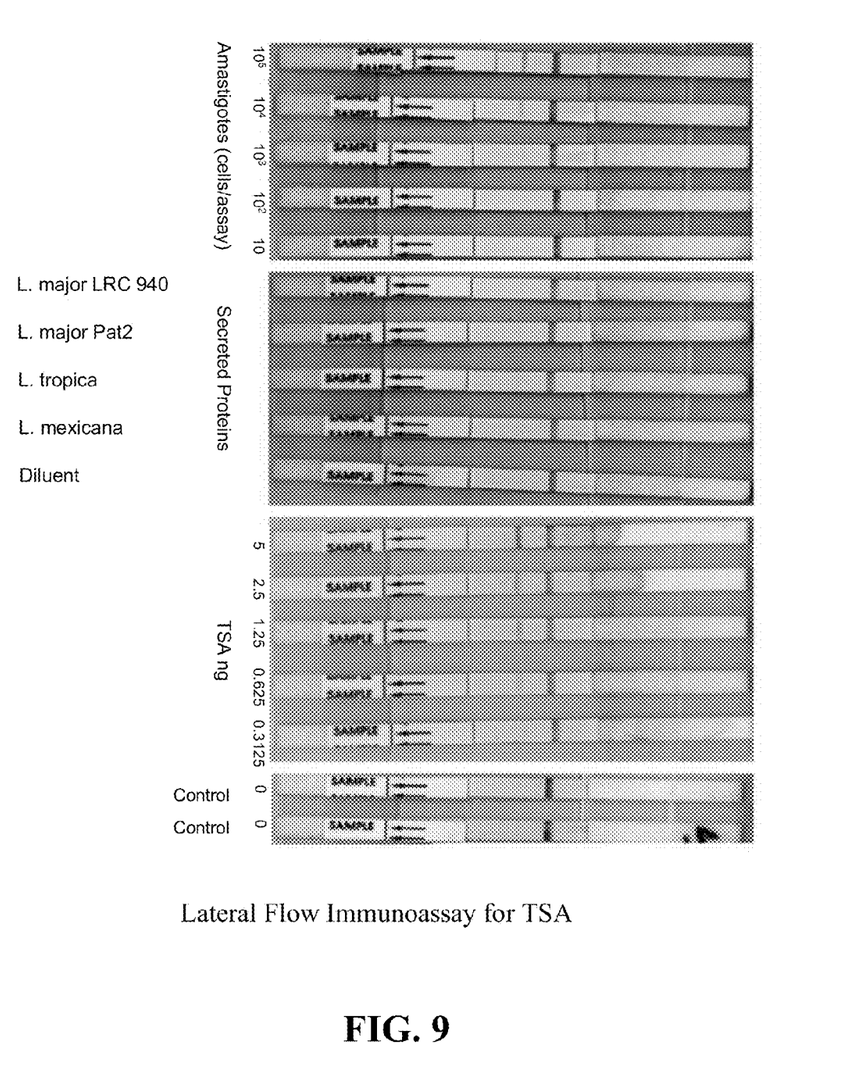
FIG. 9 shows the reactivity of a lateral flow assay for TSA and its ability to detect low cell numbers of protein emanating from amastigotes of L. major as well as recombinant TSA but not with exoantigens of various Leishmania spp.

A lateral flow immunoassay was constructed as shown in FIG. 1. C11C antibody was coated on the membrane at a concentration of 1 mg/ml as the test line. Colloidal gold conjugate was prepared by diluting rabbit anti-TSA and adding to gold salt. After incubation, 5% BSA was added as a blocking reagent. Following mixing, the gold-antibody conjugate was concentrated by spinning down and discarding the supernatant. The gold was diluted to the appropriate OD at 520-540 nm using gold suspension buffer and stabilizers, and used at an OD of 12. The antibody-gold conjugate was then sprayed onto the conjugate pad. The control line was recombinant Protein A sprayed at a concentration of 1 mg/ml. Antigens or solubilized amastigotes or promastigotes (20 ul) were applied to the sample pad followed by 3 drops of chase buffer (PBS plus 0.1% sodium azide). The lateral flow was evaluated with varying dilutions of TSA, L. major amastigotes and promastigotes, and secreted proteins produced in culture from various leishmania spp. FIG. 9 shows the reactivity of amastigotes and promastigotes in a lateral flow assay for TSA as described in Example 5.

Example 6

Sandwich ELISA and Lateral Flow Immunoassay for Identifying WIC79.3 Antigen in L. major Promastigotes and Secreted Proteins A monoclonal antibody known as WIC79.3, (available from WRAIR) were evaluated for use in assays. This antibody has been shown to be specific for L. major lipophosphoglycan (LPG) (Kelleher et al. Proc. Natl. Acad. Sci. USA 89:6-10, 1992; de Ibarra et al. Parasitology 85:523-31, 1982; Greenblatt et al. J. Clin. Microbiol. 18:191-3, 1983; Handman et al. EMBO J. 1984; 3(10): 2301-6, 1984).

Figure 10:
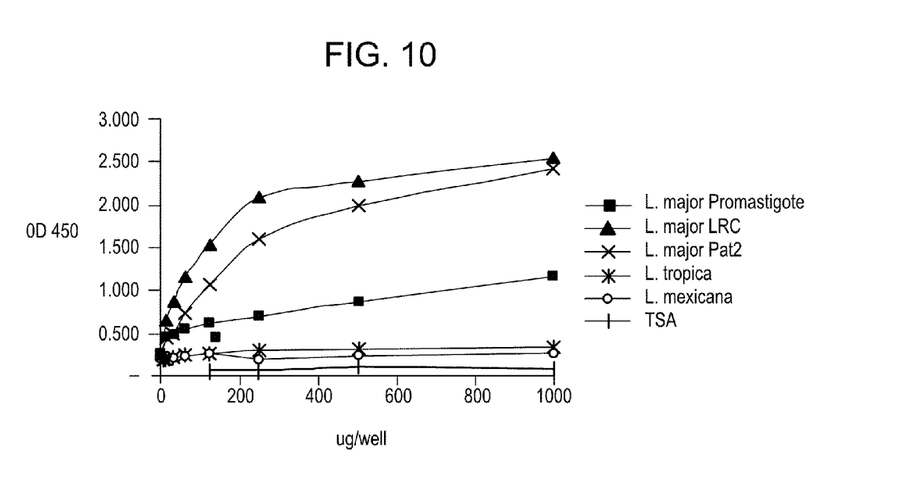
FIG. 10 shows the ability of the monoclonal antibody WIC79.3 to detect L. major secreted proteins as well as whole L. major promastigotes.

Initial studies using the WIC79.3 monoclonal antibody with secreted proteins from various Leishmania spp. as solid phase in an ELISA assay indicated that this antibody detects an antigen in L. major secreted proteins, as well as in whole L. major promastigotes, more effectively than in L. tropica and L. mexicana. In addition, this antigen was not detectable in L. major amastigotes. Further analysis was then performed using a WIC79.3 sandwich ELISA in which WIC79.3 was used as both the solid phase antigen and as detection antibody to detect secreted proteins. In this study the antibody was biotinylated and the assay developed using avidin HRP and TMB as substrate. The data is shown in FIG. 10.

Figure 11:
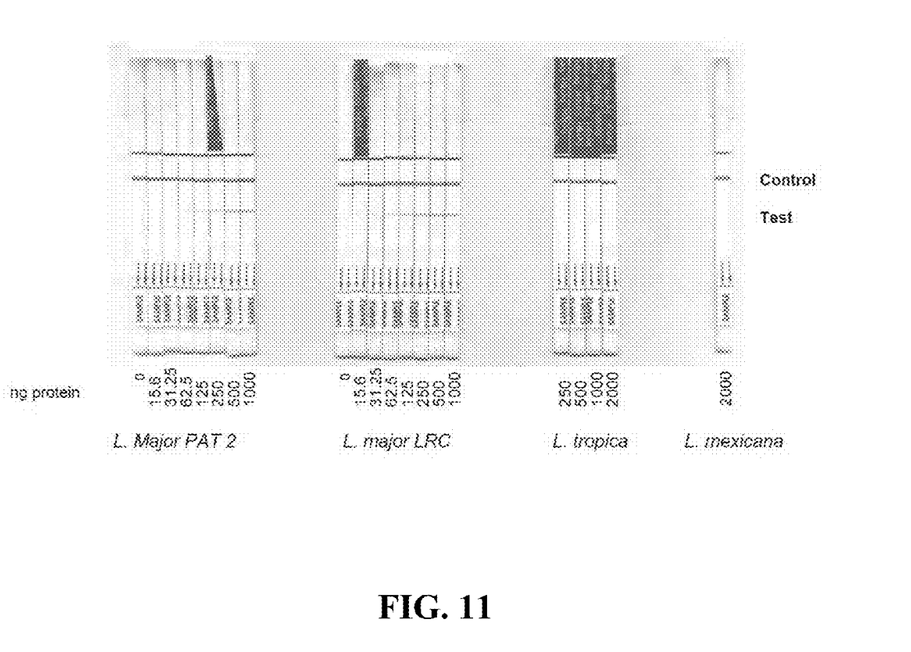
FIG. 11 shows the ability of a lateral flow assay employing the antibody WIC79.3 to detect L. major secreted proteins, or exoantigens, but not L. tropica or L. mexicana in the same concentration range.

A lateral flow assay using the WIC79.3 antibody was also developed using the techniques described above. As shown in FIG. 11, this assay was found to be capable of detecting L. major exoantigens and thus has the potential to be used for specific identification of secreted antigens in samples taken from skin lesions.

From the foregoing, it will be appreciated that, although specific embodiments of the invention have been described herein for the purpose of illustration, various modifications may be made without deviating from the spirit and scope of the invention.

SEQ ID NO: 1 and 2 are set out in the attached Sequence Listing. The codes for polynucleotide and polypeptide sequences used in the attached Sequence Listing confirm to WIPO Standard ST.25 (1988), Appendix 2.

All references disclosed herein, including patent references and non-patent references, are hereby incorporated by reference in their entirety as if each was incorporated individually.

We claim:

1. A method for detecting cutaneous leishmaniasis in a biological sample, comprising:
   (a) contacting the biological sample with a polyclonal antibody specific for a polypeptide of SEQ ID NO: 1 to form an antibody-polypeptide conjugate, wherein the polyclonal antibody is labeled with a reporter agent;
   (b) contacting the antibody-polypeptide conjugate with a monoclonal antibody specific for a polypeptide of SEQ ID NO: 1 in order to capture the antibody-polypeptide conjugate, wherein the monoclonal antibody is raised against L. major amastigotes; and
   (c) detecting the presence of the antibody-polypeptide conjugate, thereby detecting cutaneous leishmaniasis in the biological sample.

2. The method of claim 1, wherein the biological sample is taken from a cutaneous lesion.

3. The method of claim 2, wherein the biological sample is selected from the group consisting of: scrapings, biopsies, and aspirates.

4. The method of claim 1, wherein the biological sample is a mammalian sample.

5. The method of claim 1, wherein the reporter agent is a colorimetric or fluorescent indicator.

6. The method of claim 5, wherein the reporter agent is selected from the group consisting of: colloidal gold and fluorescent dyes.

7. The method of claim 1, wherein the monoclonal antibody is specific for a conformational epitope of the polypeptide of SEQ ID NO: 1 that is present in both amastigotes and promastigotes.

8. The method of claim 1, wherein the presence of the polypeptide of SEQ ID NO: 1 is detected by means of ELISA.

9. The method of claim 1, wherein the monoclonal antibody is immobilized on a solid support.

10. The method of claim 9, wherein the solid support is a nitrocellulose membrane.

11. A method for detecting cutaneous leishmaniasis in a biological sample, comprising:

(a) contacting the biological sample with a monoclonal antibody specific for a polypeptide of SEQ ID NO: 1 to form an antibody-polypeptide conjugate, wherein the monoclonal antibody is raised against *L. major* amastigotes and wherein the monoclonal antibody is labeled with a reporter agent;

(b) contacting the antibody-polypeptide conjugate with a polyclonal antibody specific for a polypeptide of SEQ ID NO: 1 in order to capture the antibody-polypeptide conjugate; and (c) detecting the presence of the antibody-polypeptide conjugate, thereby detecting cutaneous leishmaniasis in the biological sample.

12. The method of claim 11, wherein the biological sample is taken from a cutaneous lesion.

13. The method of claim 12, wherein the biological sample is selected from the group consisting of: scrapings, biopsies, and aspirates.

14. The method of claim 11, wherein the biological sample is a mammalian sample.

15. The method of claim 11, wherein the reporter agent is a colorimetric or fluorescent indicator.

16. The method of claim 15, wherein the reporter agent is selected from the group consisting of: colloidal gold and fluorescent dyes.

17. The method of claim 11, wherein the monoclonal antibody is specific for a conformational epitope of the polypeptide of SEQ ID NO: 1 that is present in both amastigotes and promastigotes.

18. The method of claim 11, wherein the presence of the polypeptide of SEQ ID NO: 1 is detected by means of ELISA.

19. The method of claim 11, wherein the polyclonal antibody is immobilized on a solid support.

20. The method of claim 19, wherein the solid support is a nitrocellulose membrane.

* * * * *

```
                              SEQUENCE LISTING

<160> NUMBER OF SEQ ID NOS: 2

<210> SEQ ID NO 1
  <211> LENGTH: 199
  <212> TYPE: PRT
  <213> ORGANISM: Leishmania Major

<400> SEQUENCE: 1

Met Ser Cys Gly Asn Ala Lys Ile Asn Ser Pro Ala Pro Ser Phe Glu
  1               5                   10                  15

Glu Val Ala Leu Met Pro Asn Gly Ser Phe Lys Lys Ile Ser Leu Ser
                  20                  25                  30

Ser Tyr Lys Gly Lys Trp Val Val Leu Phe Phe Tyr Pro Leu Asp Phe
              35                  40                  45

Ser Phe Val Cys Pro Thr Glu Val Ile Ala Phe Ser Asp Ser Val Ser
      50                  55                  60

Arg Phe Asn Glu Leu Asn Cys Glu Val Leu Ala Cys Ser Ile Asp Ser
  65                  70                  75                  80

Glu Tyr Ala His Leu Gln Trp Thr Leu Gln Asp Arg Lys Lys Gly Gly
                  85                  90                  95

Leu Gly Thr Met Ala Ile Pro Met Leu Ala Asp Lys Thr Lys Ser Ile
              100                 105                 110

Ala Arg Ser Tyr Gly Val Leu Glu Glu Ser Gln Gly Val Ala Tyr Arg
          115                 120                 125

Gly Leu Phe Ile Ile Asp Pro His Gly Met Leu Arg Gln Ile Thr Val
      130                 135                 140

Asn Asp Met Pro Val Gly Arg Ser Val Glu Glu Val Leu Arg Leu Leu
  145                 150                 155                 160

Glu Ala Phe Gln Phe Val Glu Lys His Gly Glu Val Cys Pro Ala Asn
                  165                 170                 175

Trp Lys Lys Gly Ala Pro Thr Met Lys Pro Glu Pro Asn Ala Ser Val
              180                 185                 190

Glu Gly Tyr Phe Ser Lys Gln
          195

<210> SEQ ID NO 2
  <211> LENGTH: 1691
  <212> TYPE: DNA
  <213> ORGANISM: Leishmania Major

<400> SEQUENCE: 2
ctgtacttta ttgccaccag ccagccatgt cctgcggtaa cgccaagatc aactctcccg        60
cgccgtcctt cgaggaggtg gcgctcatgc ccaacggcag cttcaagaag atcagcctct       120
cctcctacaa gggcaagtgg gtcgtgctct tcttctaccc gctcgacttt agcttcgtgt       180
gcccgacaga ggtcatcgcg ttctccgaca gcgtgagtcg cttcaacgag ctcaactgcg       240
aggtcctcgc gtgctcgata gacagcgagt acgcgcacct gcagtggacg ctgcaggacc       300
gcaagaaggg cggcctcggg accatggcga tcccaatgct agccgacaag accaagagca       360
tcgctcgttc ctacggcgtg ctggaggaga gccagggcgt ggcctaccgc ggtctcttca       420
tcatcgaccc ccatggcatg ctgcgtcaga tcaccgtcaa tgacatgccg gtgggccgca       480
```

```
                                                        -continued gcgtggagga ggttctacgc ctgctggagg cttttcagtt cgtggagaag cacggcgagg    540
tgtgccccgc gaactggaag aagggcgccc ccacgatgaa gccggaaccg aatgcgtctg    600
tcgaaggata cttcagcaag cagtaaacct gtgagcgtcg caggagtcag tgtgacctca    660
cccgcctctg ccagtgggtg cgagagggcg tgagggattg tgggaaggct gttggatatg    720
atgcagacag cgatgaatgc aactcccaca cactggccct cctcagccct ctccacacag    780
acacacgcac gcatgtgcgg tgcttctgct ccttcatttc ctgatgcggt ttctttacta    840
tttatgtttt cccctgtttt ggtttcgcgg aatatggacg cacgaacgca gagagcagag    900
gcgcgacaca cacacgggg gcgcacacgt gtaagcgacg gagcgcgaca cagaggggag     960
aagccggaaa ggatatatga aatgaagatg gtgtcccgca cacacaggca cgcacacggg   1020
gcgaacgcgt ggcgcgtcct ttctatggtt tcgctgctgc tgttcgtgtt ctcgcttcgc   1080
tggttgcagt tccggctcgt gctgccctgc ctgccactct tggtccgtgt ctgtccgtgt   1140
ccgtgtccgt gtggggggg gagagttttt cactcccccg gtcacctcta ctgtttatta   1200
tttatatgtt tatttatttc catattgact caattcattc cgtgcgaaag ccggcttgtt   1260
ccggcgtctt ttgacgaaca actgccctat cagctggtga tggccgtgta gtggactgcc   1320
atggcgttga cgggagcggg ggattagggt tcgattccgg agagggagcc tgagaaatag   1380
ctaccacttc tacggagggc agcaggcgcg caaattgccc aatgtcaaaa caaaacgatg   1440
aggcagcgaa aagaaataga gttgtcagtc catttggatt gtcatttcaa tgggggatat   1500
ttaaacccat ccaatatcga gtaacaattg gaggacaagt ctggtgccag cacccgcggt   1560
aattccagct ccaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaaa a                                                       1691
```